United States Patent
Perkins

(10) Patent No.: US 6,627,176 B2
(45) Date of Patent: Sep. 30, 2003

(54) METAL COMPLEXES FOR USE IN MEDICAL AND THERAPEUTIC APPLICATIONS

(75) Inventor: Christopher Mark Perkins, Cincinnati, OH (US)

(73) Assignee: Procter & Gamble Company, Cincinnati, OH (US)

( * ) Notice: Subject to any disclaimer, the term of this patent is extended or adjusted under 35 U.S.C. 154(b) by 105 days.

(21) Appl. No.: 09/957,159

(22) Filed: Sep. 20, 2001

(65) Prior Publication Data

US 2002/0041846 A1 Apr. 11, 2002

Related U.S. Application Data

(60) Provisional application No. 60/235,012, filed on Sep. 25, 2000.

(51) Int. Cl.[7] .............................. A61K 51/00; C07F 5/00
(52) U.S. Cl. ...................................... 424/1.65; 534/10
(58) Field of Search ......................... 424/1.65; 534/10, 534/11, 12, 13, 14, 15; 540/450, 465

(56) References Cited

U.S. PATENT DOCUMENTS

| | | | |
|---|---|---|---|
| 5,409,689 A | | 4/1995 | Winchell et al. |
| 5,593,659 A | | 1/1997 | Winchell et al. |
| 5,645,818 A | | 7/1997 | Jackels et al. |
| 5,693,324 A | | 12/1997 | Edwards |
| 5,874,573 A | * | 2/1999 | Winchell et al. ............ 540/465 |
| 6,056,939 A | | 5/2000 | Desreux et al. |
| 6,093,382 A | | 7/2000 | Wedeking et al. |
| 6,225,464 B1 | * | 5/2001 | Hiler, II et al. ............ 540/450 |

FOREIGN PATENT DOCUMENTS

| | | | | |
|---|---|---|---|---|
| WO | WO 94/04485 | * | 3/1994 | ......... C07F/229/76 |
| WO | WO 98/39335 | * | 9/1998 | ......... C07D/487/08 |
| WO | WO 00/43004 | | 7/2000 | |

OTHER PUBLICATIONS

Broan, Christopher et al: "Structure and solution stability of indium and gallium complexes of 1,4,7–triazacyclononan-etriacetate and of yttrium complexes for use in imaging and radioimmunotherapy. X–ray molecular structure of the I". J. Chem. Soc., Perkin Trans. 2, No. 1, 1991, pp. 87–99, XP001031171p.87.

. Cox, Jonathan P. L. et al "Synthesis of a kinetically sstable yttrium–90 labeled macrocycle–antibody conjugate" J. Chem. Soc., Chem. Commun. No. 12, 1989, pp. 797–798, XP001031170 the whole document.

. Hubin, Timothy J. et al: Ultra rigid cross–bridged tet-raazamacrocycles as ligands–the challenge and the solution Chem. Commun. (Cambridge), No. 16, 1998, pp. 16–1676, XP001039648 the whole document.

Weisman, Gary R. etal: "Synthesis and transition–metal complexes of new cross–bridged tetraamine ligands" Chem. Commun. (Cambridge), No. 8, 1996, p. 947–948, xp001031187 the whole document.

Pirtluigi Barbaro,Synthesis and characterization of the tet-raazamacrocycle 4, 10–dimethyl–1,4,7,10–tetraazacy-clododecane–1,7–diacetic acid ($H_2Me_2DO2A$) and of its neutral copper (11) complex $Cu(Me_2DO2A)$. A new $^{64}Cu$–labeled macrocyclic complex position emission tomography imaging. J. Chem. Soc. Dalton, $28^{th}$ Mar. 2000, 2393–2401. Firenze, Italy.

* cited by examiner

*Primary Examiner*—Michael G. Hartley
(74) *Attorney, Agent, or Firm*—James F. McBride; Kim W. Zerby; Steve W. Miller

(57) ABSTRACT

The first aspect of the present invention relates to transition metal complexes having the formula:

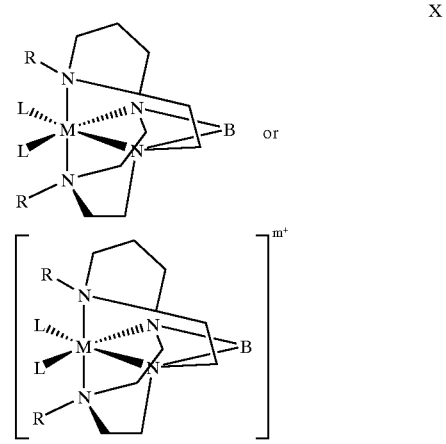

wherein M is a radioactive metal having a valence of +2, +3, +4, or +5; $m^+$ designates the charge of the metal complex, each R is independently $C_1-C_8$ linear or branched alkyl, a fifth ligand, and mixtures thereof; B is a bridging unit which comprises at least 2 carbon atoms; L is a pharmaceutically acceptable ligand; X is a pharmaceutically compatible anion in sufficient amount to provide electronic neutrality. The complexes of the present invention are suitable for use in diagnostic, therapeutic or radiotherapeutic or chemotherapeutic compositions for visualization, therapy, chemotherapy or radiotherapy of tissues or organs.

28 Claims, No Drawings

METAL COMPLEXES FOR USE IN MEDICAL AND THERAPEUTIC APPLICATIONS

This Application claims priority to U.S. Provisional Patent Application Ser. No. 60/235,012 filed Sep. 25, 2000.

FIELD OF THE INVENTION

The present invention relates to radioactive metal complexes which comprise a radioactive metal chelated by a ligand, inter alia, a substituted 1,4,8,1 1-tetraazabicyclo [6.6.2] hexadecane, a substituted 1,4,8,11-tetraazabicyclo [6.6.4] octadec-16-ene. The compounds of the present invention are suitable for use in radiodiagnostic compositions, radiotherapy, neutron capture therapy, and for chemotherapy. The diagnostic and therapeutic compositions of the present invention can further comprise one or more adjunct ingredients.

BACKGROUND OF THE INVENTION

Nuclear medicine procedures and treatments are based on internally distributed radioactive materials, such as radiopharmaceuticals or radionuclides, which emit electromagnetic radiations as gamma rays or photons. Following adequate administration, inter alia, intravenous injection, orally, inhalation, the gamma rays are readily detected and quantified within the body using instrumentation such as scintillation and gamma cameras. The gamma-emitting agents localize themselves into particular targeted tissue depending upon the characteristics of the radiopharmaceutical or radionuclide complex. Once localized, these agents yield either high signal intensity or a high radiation dose, as in the case of radiotherapeutics.

The use of neutron capture therapy for the treatment of cancer is accomplished by administering a target substance which emits short-range radiation when irradiated by neutrons. $^{10}$B (boron-10) and $^{157}$Gd (gadolinium-157) are commonly used radionuclides, the latter having a very high cross section for neutrons and is capable of emitting short range Auger-electrons. In the past neutron capture therapy has suffered from insufficient concentration of target substance in the desired cells and in the case of gadolinium, has suffered from the exclusion of the gadolinium from the inside of the cell.

There is a long felt need in the art for a ligand which is modifiable, forms a very stable complex, and which can suitably transport radioactive metals to target tissues. There is a need for a ligand/metal complex which can deliver sufficient gamma emitting material to tumor cells and other selected tissue to enhance radiotherapy techniques. There is also a need for a strongly binding ligand to concentrate radionuclides to target tissues.

SUMMARY OF THE INVENTION

The present invention meets the aforementioned needs in that it has been surprisingly discovered that certain radioactive transition metal complexes, inter alia, substituted 1,4,8,11-tetraazabicyclo[6.6.2] hexadecane transition metal complexes, are suitable for use as radiopharmaceuticals and radionuclides in medical radiotherapy. The ligands of the present invention can be varied to provide the proper affinity for different cell types, inter alia, tumor cells, organ tissue. The ligands of the present invention provide a very stable radionuclide complex thereby preventing the loss of radioactive metal through pre-mature release due to hydrolysis or metal oxide formation. The surprising stability of the complexes of the present invention in vivo insures delivery of the desired nuclide to the desired tissue in the desired amount thereby overcoming decreased efficacy and loss of targeting discrimination.

The first aspect of the present invention relates to transition metal complexes having the formula:

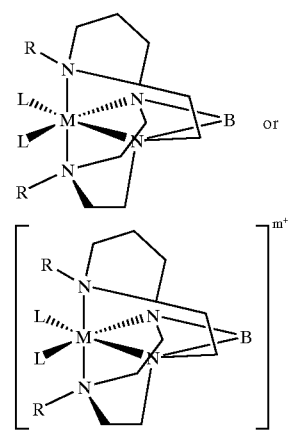

wherein M is a radioactive metal having a valence +2, +3, +4, or +5, $m^+$ designates the charge of the metal complex, each R is independently $C_1-C_8$ linear or branched alkyl, a fifth ligand, and mixtures thereof; B is a bridging unit which comprises at least 2 carbon atoms; L is a pharmaceutically acceptable ligand; X is a pharmaceutically compatible anion in sufficient amount to provide electronic neutrality.

The present invention further relates to a diagnostic, therapeutic or radiotherapeutic or chemotherapeutic composition for visualization, therapy, chemotherapy or radiotherapy of tissues or organs comprising:

a) an effective amount, preferably from about 0.05 mmol, more preferably from about 0.1 mmol, most preferably from about 1 mmol to about 100 mmole, preferably to about 50.0 mmol, more preferably to about 25.0 mmol, most preferably to about 10 mmol per liter, or alternatively from about 0.01 micro Currie ($\mu$Ci), preferably from about 0.1 $\mu$Ci, more preferably from about 1 $\mu$Ci, most preferably from about 10 $\mu$Ci to about 200 $\mu$Ci, preferably to about 100 $\mu$Ci, more preferably to about 50 $\mu$Ci, most preferably to about 25 $\mu$Ci, of a transition metal radionuclide complex having the formula:

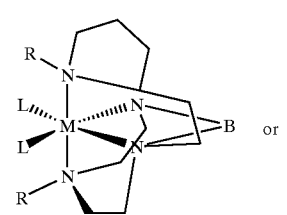

-continued

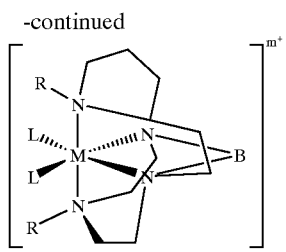

wherein M is a radioactive metal having a valence of +2, +3, +4, or +5; each R is independently $C_1$–$C_8$ linear or branched alkyl, a fifth ligand, and mixtures thereof; B is a bridging unit which comprises at least 2 carbon atoms; L is a pharmaceutically acceptable ligand; X is a pharmaceutically compatible anion in sufficient amount to provide electronic neutrality; and b) the balance a pharmaceutically acceptable carrier and other adjunct ingredients.

The present invention also relates to methods for providing radiochemical therapy. One aspect of these methods is a method which comprises the steps of:

a) administering to tissue either in vitro or in vivo an effective amount of a transition metal complex according to the present invention which is capable of emitting short-range radiation when irradiated by neutrons; and b) irradiating said tissue with a source of neutrons.

A further aspect of the methods of the present invention relates to a method comprising the step of: contacting tissue with an effective amount of a transition metal complex according to the present invention which is capable of emitting radiation.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to transition metal complexes comprising a transition metal and ligand wherein said transition metal is a radioactive element having a valence of +2, +3, +4, or +5. The radioactive metal is chelated by a suitable ligand, non-limiting examples of which include substituted 1,4,8,11-tetraazabicyclo[6.6.2] hexadecane, substituted 1,4,8,11-tetraazabicyclo[6.6.4] octadec-16-ene, and the like described herein below. The complexes of the present invention are suitable for use as a radiopharmaceutical and as a radionuclide. The complexes of the present invention are suitable for use in the treatment of tissue, inter alia, for enhancing the contrast image of tissue, for use in killing targeted tissue.

One aspect of the present invention relates to the complexes of the present invention as radiotherapeutic agents and in this sense the complex functions as a radionuclide. For example, the complexes of the present invention can be used as neutron capture agents wherein the complex is delivered to a desired tissue, organ, or type or tissue, inter alia, tumor cells, and said site of delivery is subsequently irradiated with a source of neutrons to achieve emission of tissue damaging particles, inter alia, Auger electrons. The complexes of the present invention can be re-radiated until sufficient tissue therapy is achieved.

Another aspect of the present invention relates to delivery of radioactive metals which emit alpha or beta particles and in this sense the complex functions as a radiopharmaceutical. The ligand portion of the complex can be modified to target (be specifically delivered to) a particular type of tissue or organ such that the organ or tissue will have enhanced affinity for the complex. In addition to imbuing specificity for an organ or tissue type, the complexes of the present invention can be adjusted, by manipulation of the ligand chemical structure, to remain in said tissue or organic for a shorter or longer period of time. For example, the presence of moieties which have increased or decreased tissue affinity can be placed onto the substituted 1,4,8,11-tetraazabicyclo [6.6.2] hexadecane or substituted 1,4,8,11-tetraazabicyclo [6.6.4] octadec-16-ene framework without pejoratively affecting the stability or radionuclear properties of the complex.

Transition Metal Complex

The transition metal complexes of the present invention comprise a radioactive transition metal and a substituted ligand. The complexes of the present invention are neutral species having the formula:

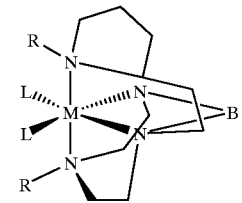

or charged species having the formula:

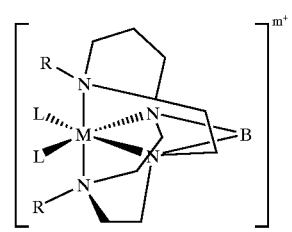

wherein M is a radioactive transition metal having a valence of +2, +3, +4, or +5; $m^+$ designates the charge of the metal complex, and X represents a pharmaceutically acceptable anion present in sufficient amount to provide electronic neutrality. Non-limiting examples of preferred radionuclides include Tc, Cu, Ru, Co, Pt, Fe, Os, Ir, W, Re, Cr, Mo, Mn, Ni, Rh, Pd, Nb, Pb, Ga, As, In, and Ta. Examples of preferred isotopes of these radionuclides include $^{99m}$Tc, $^{62}$Cu, $^{64}$Cu, $^{67}$Cu, $^{203}$Pb, $^{67}$Ga, $^{68}$Ga, $^{72}$As, $^{111}$In, $^{113m}$In, $^{97}$Ru, $^{52}$Fe, $^{52m}$Mn, $^{51}$Cr, $^{57}$Co, $^{186}$Re, $^{188}$Re, $^{90}$Y, $^{153}$Sm, $^{140}$La, $^{212}$Bi, $^{169}$Yb, $^{225}$Ac. More preferred radionuclides are selected from the group consisting of $^{99m}$Tc, $^{64}$Cu, $^{67}$Cu, $^{186}$Re, $^{188}$Re, and $^{111}$In.

Each R is independently $C_1$–$C_8$ linear or branched alkyl, a fifth ligand, and mixtures thereof, preferably R is methyl, ethyl, isopropyl, butyl, and mixtures thereof.

As described herein above, each R can optionally comprise a fifth ligand. For the purposes of the present invention the term "further ligand site" is defined herein as a "moiety which occupies a ligand site on the metal" that is, replaces an L moiety as defined herein below. Non limiting example of further ligand sites include —$(CH_2)_nCO_2^{31}$, wherein the index n has the value from 1 to about 10, preferably from 1 to 4, more preferably the index n is 1 or 2. When R is a fifth ligand it will take the place of one L unit as defined herein. Further examples of ligand sites include heteroatom substituted alkyl, alkylenearyl, alkylene heteroaryl, and the like, for example, hydroxyethyl, 2-furanyl, 2-pyridylmethyl, 2-hydroxybenzyl, alkyl imidazole. For the purposes of R as a fifth ligand, the term "alkyl" is defined herein as a $C_1$–$C_8$ linear or branched alkyl unit, preferably methyl, ethyl, n-propyl, isopropyl, n-butyl, and mixtures thereof.

B is a bridging unit comprising at least 2 carbon atoms. The ligands of the present invention have the formula:

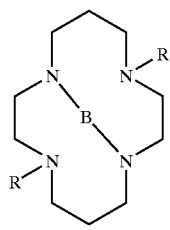

wherein said R units are defined herein above. Preferred B units are substituted or unsubstituted $C_2$–$C_4$ alkylene, substituted or unsubstituted $C_2$–$C_4$ alkenylene, substituted or unsubstituted $C_8$–$C_{22}$ alkylenearyl, and mixtures thereof. Non limiting examples of preferred B units are ethylene, propylene, 2-butenylene, 2,3-dimethylbutenylene, 1,2-xylyl (ortho-xylyl), 4-substituted 1,2-xylyl, and mixtures thereof. For the purposes of the present invention as it applies to B units, the term "substituted" is defined herein as a $C_1$–$C_8$ linear or branched alkyl units which can be substituted along alkylene, alkenylene, or alkylenearyl units; preferably methyl, ethyl, n-propyl, isopropyl, n-butyl, and mixtures thereof.

An example of a preferred B unit which is an alkylene moiety has the formula:

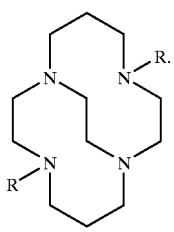

An example of a preferred B unit which is an alkenylene moiety has the formula:

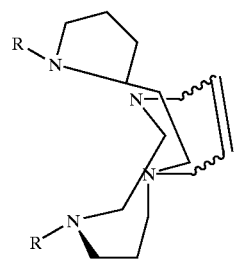

which forms a transition metal complex having the formula:

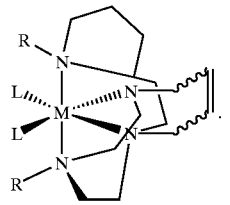

X

An example of a preferred B unit which is an alkenylenearyl moiety has the formula:

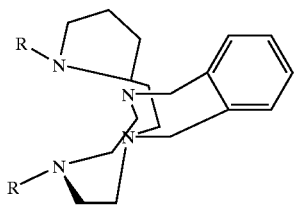

which forms a transition metal complex having the formula:

X

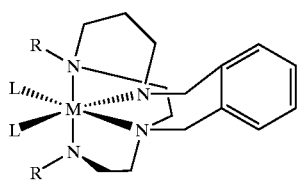

L is a pharmaceutically acceptable ligand, non-limiting examples of which include halogen, hydroxide, or water. Those of ordinary skill in the art will recognize that because of the relative instability of the radiopharmaceutical, the radionuclide may be formed prior to use and therefore the complex obtained prior to administration. In this case and in others the preferred carrier is water because of its ubiquitous nature relative to tissue content. The complexes of the present invention may be formed as the bis halo complex, but upon dissolution in the pharmaceutical carrier, the necessary exchange reaction and salt formation will occur, therefore, X is any suitable anion in sufficient amount to provide electronic neutrality. Non-limiting examples of preferred anions include halogen, preferred halogen is $Cl^-$, $OH^-$, $BF_4^-$, $PF_6^-$, $RCO_2^-$, $R'SO_3^-$, $R'SO_4^-$, $ClO_4^-$, and mixtures thereof. The following is an example of a complex which is formed as bischloro-1,4,8,11-tetraazabicyclo[6.6.2] hexadecane copper (II) which when added to the aqueous pharmaceutical carrier and excipients forms a water soluble according to the scheme:

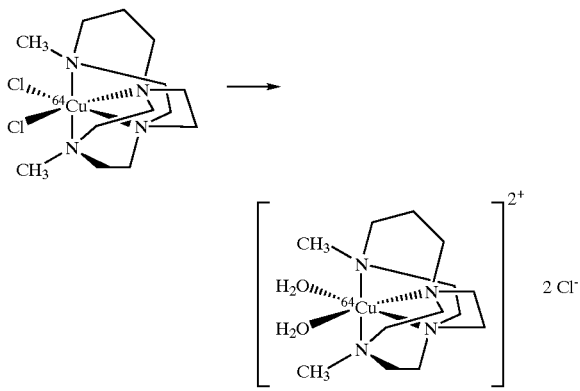

wherein the anionic chloro ligands are replaced by neutral water molecules.

The following are examples of complexes comprising a fifth ligand site.

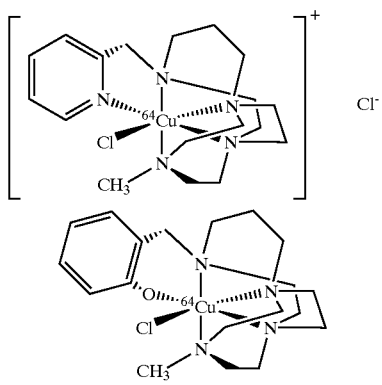

Another aspect of the present invention relates to the simultaneous use of two different metal ions for imaging and/or therapy. For example, $Gd^{3+}$ and $Dy^{3+}$ chelated by the same ligand can be injected simultaneously to increase the contrast of MRI images or a $Gd^{3+}$ complex can be injected intravenously simultaneously with an oral administration of super paramagnetic iron oxide particle. In radiopharmacy, the simultaneous used of radio isotopes such as $^{111m}In$ and $^{90}Y$ has been described but these isotopes were located in different complexes of the same ligand. The present invention is directed to ligands which form discrete, stable and water-soluble heteropolymetallic species of well-known stoichiometry. The stability and the molecular weight of these complexes are well-controlled by grafting in the same molecule two totally different complexing units aimed at achieving a selective coordination of metal ions with totally different steric requirements.

FORMULATIONS

The compositions of the present invention may be supplied as a solution, for example, in the from of a physiological solution, or in a buffer solution. If desired by the formulator, the compositions can be stabilized by the addition of antioxidants, stabilizers, etc., non-limiting examples of which include ascorbic acid, gentisic acid, or salts thereof.

The radiodiagnostic compositions of the present invention can be formulated for administration with a biologically acceptable carrier medium. In one preferred embodiment of the present invention, the carrier medium comprises sterile, pyrogen-free phosphate buffered saline (PBS). The radioactive complexes of the present invention are delivered to tissue in an effective amount. Typically, only a trace amount, from about $1 \times 10^{-12}$ M is sufficient depending upon the nuclide. The compositions of the present invention comprise an effective amount, preferably from about 0.05 mmol, more preferably from about 0.1 mmol preferably to about 2.0 mmol, more preferably to about 1.0 mmol per liter, or alternatively from about 0.01 micro Currie ($\mu$Ci), preferably from about 0.1 $\mu$Ci, more preferably from about 1 $\mu$Ci, most preferably from about 10 $\mu$Ci to about 40 $\mu$Ci, preferably to about 30 $\mu$Ci, more preferably to about 20 $\mu$Ci, most preferably to about 15 $\mu$Ci, of a transition metal radionuclide complex. Non-limiting examples of the variability of dosing levels depending upon the selected radionuclide and application thereof include:

a) about 2–200 $\mu$Ci rhenium, for example in radiotherapy;

b) about 10–60 $\mu$Ci technetium, for example in imaging.

Rhenium is particularly useful as a radiotherapy agent. The rhenium employed for the metal complexes of the present invention is preferably one of the radionuclides $^{186}Re$ or $^{188}Re$, or mixtures thereof. However, some $^{185}Re$ or $^{187}Re$ may be present in the admixture.

Technetium is particularly useful as a radionuclide for use in diagnostic imaging complexes of the present invention. Preferred technetium is one of more of $^{99m}Tc$, $^{94m}Tc$, $^{96}Tc$, or mixtures thereof, preferably $^{99m}Tc$. This isotope has a 140 keV γ-photon is ideal for use with widely-available gamma cameras and the 6 hour half-life is desirable when considering patient dosimetry.

One of the preferred formulations of the present invention relates to delivery of the complexes of the present invention in the form of a kit. A non-limiting example of a single-vial kit of the present invention comprises the radioactive transition metal complex and a source of a pharmaceutically acceptable reducing agent such as a stannous salt. Preferably, in addition, the kit is buffered with a pharmaceutically acceptable acid or base to adjust the pH to a desired value for complex formation. It is preferred that the kit contents be in lyophilized form, Such a single vial kit may optionally contain exchange ligands such as glucohheptonate, gluconate, mannitol malate, citrate or tartaric acid and may also comprise reaction modifiers, such as diethylenetriaminepentaacetic acid or ethylenediamineteraacetic acid. Additional additives, such as solublizers (for example, cyclodextrins), antioxidants (ascorbic acid) and/or fillers (for example, NaCl) may be employed to improve the radiochemical purity and stability of the final product, or to aid in the production of the kit.

In another embodiment of the formulations of the present invention are multi-vial kits. Multi-vial kits can comprise, in a first vial, the components, other than the radionuclide itself, inter alia, $^{99m}Tc$, $^{64}Cu$, $^{67}Cu$, $^{186}Re$, $^{188}Re$, or $^{111}In$. Other ingredients which comprise the first via include any component required to form a labile radionuclide complex, inter alia, a ligand according to the present invention, any necessary exchange ligands, pharmaceutically acceptable reducing agent. A preferred reducing agent includes stannous salts. The second vial comprises the radionuclide in a stable form, as well as, optional ingredients, inter alia, buffers.

In all instances, any substance used in formulating the compositions of the present invention should be virus-free, pharmaceutically pure, and substantially non-toxic in the amount delivered. The formulator may include in the compositions of the present invention various anti- bacterial or anti-fungal agents, inter alia, parabens, chlorobutanol, phenol, surbic acid, and thimerosal. Isotonic agents, glucose, inter alia, may also be included.

The radionuclide complexes and the compositions which comprises said complexes can be administered parenterally, intravenously, or by any means suitable for delivery of said complexes to the target tissue.

For radiopharmaceutical or radiotherapy formulations it is convenient to prepare the self-assembling radioactive metal complexes of the present invention at, or near, the site where they are to be used. A single, or multi-vial kit that contains all of the components needed to prepare the complexes of the present invention, other than the radionuclide ion itself is an integral part of this invention.

The amount administered may be selected based on the desired use, such as to produce a diagnostic image of an organ or other site of a subject or a desired radiotherapeutic effect, by methods known by those skill in the art.

METHOD OF USE

The present invention further relates to a method for providing a diagnostic, therapeutic or radiotherapeutic or chemotherapeutic composition for visualization, therapy, chemotherapy or radiotherapy of tissues or organs comprising the steps of administering a composition comprising:

a) an effective amount, preferably from about 0.05 mmol, more preferably from about 0.1 mmol, preferably to about 2.0 mmol, more preferably to about 1.0 mmol per liter, or alternatively from about 0.01 micro Currie ($\mu$Ci), preferably from about 0.1 $\mu$Ci, more preferably from about 1 $\mu$Ci, most preferably from about 10 $\mu$Ci to about 40 $\mu$Ci, preferably to about 30 $\mu$Ci, more preferably to about 20 $\mu$Ci, most preferably to about 15 $\mu$Ci, of a radionuclide having the formula:

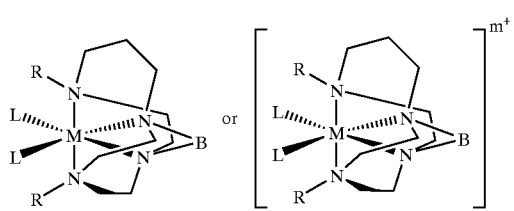

wherein M is a radioactive metal having a valence of +2 or +3; $m^+$ designates the charge of the metal complex, each R is independently $C_1$–$C_8$ linear or branched alkyl, —$(CH_2)_nCO_2^-$, a fifth ligand, and mixtures thereof; B is a bridging unit which comprises at least 2 carbon atoms; L is a pharmaceutically acceptable ligand; the index n has the value from 0 to about 10; X is a pharmaceutically compatible anion in sufficient amount to provide electronic neutrality; and b) the balance a pharmaceutically acceptable carrier and other adjunct ingredients.

EXAMPLE 1

Preparation of dichloro 4,11-dimethyl-1,4,8,11-tertaaza-bicyclo[6.6.2]hexadecane $^{64}$Cu (II)

To a 100 mL reaction flask is charged anhydrous acetonitrile (50 mL) and 4,11-diethyl-1,4,8,11-tetraaza-bicyclo [6.6.2]hexadecane (1.4 g, 5 mmol). $^{64}$CuCl$_2$ (4.7 mmol) is added and the reaction is refluxed for 3 hours. The resulting solution is filtered through glass-fiber filter paper. The resulting filtrate is concentrated under reduced pressure at 45° C. to afford a solid. The solid is suspended in toluene (50 mL) and the resulting dark supernatant is discarded. Treatment with toluene is repeated five times. The resulting solid is dried under vacuum to yield dichloro 4,11-diethyl-1,4,8, 11-tetraaza-bicyclo[6.6.2]hexadecane $^{64}$Cu.

What is claimed is:

1. A transition metal complex having the formula:

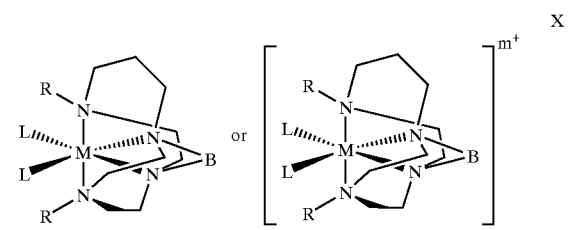

wherein M is a radioactive metal having a valence of +2 or +3; $m^+$ designates the charge of the metal complex, each R is independently $C_1$–$C_8$ linear or branched alkyl, a fifth ligand, and mixtures thereof; B is a bridging unit selected from the group consisting of 2-butenylene, 2,3-dimethylbutenylene, 1,2-xylyl, substituted 1,2-xylyl, and mixtures thereof; L is a pharmaceutically acceptable ligand; X is a pharmaceutically compatible anion in sufficient amount to provide electronic neutrality.

2. A complex according to claim 1 wherein M is a radionuclide selected from the group consisting of Tc, Cu, Ru, Co, Pt, Fe, Os, Ir, W, Re, Cr, Mo, Mn, Ni, Rh, Pd, Nb, Pb, Ga, As, In, Ta, and mixtures thereof.

3. A complex according to claim 2 wherein said radionuclide is an isotope selected from the group consisting of $^{99m}$Tc, $^{62}$Cu, $^{64}$Cu, $^{67}$Cu, $^{203}$Pb, $^{67}$Ga, $^{68}$Ga, $^{72}$As, $^{111}$In, $^{113m}$In, $^{97}$Ru, $^{52}$Fe, $^{52m}$Mn, $^{51}$Cr, $^{57}$Co, and mixtures thereof.

4. A complex according to claim 3 wherein said isotope is $^{99m}$Tc, $^{64}$Cu, $^{67}$Cu, $^{111}$In, and mixtures thereof.

5. A complex according to claim 1 wherein R is methyl, ethyl, isopropyl, butyl, and mixtures thereof.

6. A complex according to claim 5 wherein R is methyl.

7. A complex according to claim 1 wherein R is a fifth ligand selected from the group consisting of —$(CH_2)_nCO_2^-$, heteroatom substituted alkyl, alkylenearyl, alkylene heteroaryl, and mixtures thereof; wherein the index n is from 1 to 10.

8. A complex according to claim 7 wherein the index n has the value of from 1 to 4.

9. A complex according to claim 8 wherein the index n has the value of 1 or 2.

10. A complex according to claim 9 wherein R is hydroxyethyl, 2-furanyl, 2-pyridylmethyl, 2-hydroxybenzyl, alkyl imidazole, and mixtures thereof.

11. A complex according to claim 1 wherein L is halogen.

12. A complex according to claim 1 wherein X is selected from the group consisting of Cl$^-$, OH$^-$, BF$_4^-$, PF$_6^-$, ClO$_4^-$, and mixtures thereof.

13. A complex according to claim 1 wherein $m^+$ has the value of 2 or 3.

14. A diagnostic, therapeutic or radiotherapeutic or chemotherapeutic composition for visualization, therapy, chemotherapy or radiotherapy of tissues or organs comprising:

a) an effective amount of a transition metal radionuclide complex having the formula:

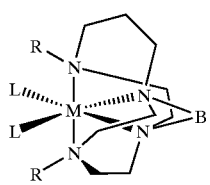

wherein M is a radioactive metal having a valence of +2, +3, +4, or +5; each R is independently $C_1$–$C_8$ linear or branched alkyl, a fifth ligand, and mixtures thereof; wherein B is a bridging unit selected from the group consisting of 2-butenylene, 2,3-dimethylbutenylene, 1,2-xylyl, substituted 1,2-xylyl, and mixtures thereof; L is a pharmaceutically acceptable ligand; X is a pharmaceutically compatible anion in sufficient amount to provide electronic neutrality; and b) the balance a pharmaceutically acceptable carrier and other adjunct ingredients.

15. A composition according to claim 14 comprising from about 0.05 mmol to about 2.0 mmol of said transition metal radionuclide complex.

16. A composition according to claim 15 comprising from about 0.1 mmol to about 1.0 mmol of said transition metal radionuclide complex.

17. A composition according to claim 14 comprising from about 0.01 µCi to about 40 µCi of said transition metal radionuclide complex.

18. A composition according to claim 17 comprising from about 0.1 µCi to about 30 µCi of said transition metal radionuclide complex.

19. A composition according to claim 18 comprising from about 1 µCi to about 20 µCi of said transition metal radionuclide complex.

20. A composition according to claim 19 comprising from about 10 µCi to about 15 µCi of said transition metal radionuclide complex.

21. A diagnostic, therapeutic or radiotherapeutic or chemotherapeutic composition for visualization, therapy, chemotherapy or radiotherapy of tissues or organs comprising:

a) an effective amount of a transition metal radionuclide complex having the formula:

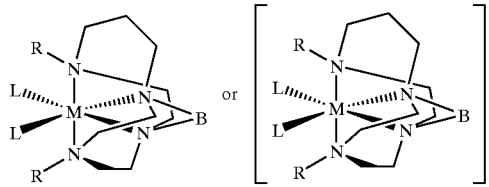

wherein M is a radioactive metal having a valence of 2, +3, +4, or +5; m⁺ designates the charge of the metal complex, each R is independently $C_1$–$C_8$ linear or branched alkyl, a fifth ligand, and mixtures thereof; wherein B is a bridging unit selected from the group consisting of 2-butenylene, 2,3-dimethylbutenylene, 1,2-xylyl, substituted 1,2-xylyl, and mixtures thereof; L is a pharmaceutically acceptable ligand; X is a pharmaceutically compatible anion in sufficient amount to provide electronic neutrality; and b) the balance a pharmaceutically acceptable carrier and other adjunct ingredients.

22. A composition according to claim 21 comprising from about 0.05 mmol to about 2.0 mmol of said transition metal radionuclide complex.

23. A composition according to claim 22 comprising from about 0.1 mmol to about 1.0 mmol of said transition metal radionuclide complex.

24. A composition according to claim 21 comprising from about 0.01 µCi to about 40 µCi of said transition metal radionuclide complex.

25. A composition according to claim 24 comprising from about 0.1 µCi to about 30 µCi of said transition metal radionuclide complex.

26. A composition according to claim 25 comprising from about 1 µCi to about 20 µCi of said transition metal radionuclide complex.

27. A composition according to claim 26 comprising from about 10 µCi to about 15 µCi of said transition metal radionuclide complex.

28. A method for providing a diagnostic, therapeutic or radiotherapeutic or chemotherapeutic composition for visualization, therapy, chemotherapy or radiotherapy of tissues or organs comprising the steps of administering a composition comprising:

a) an effective amount of a transition metal radionuclide complex having the formula:

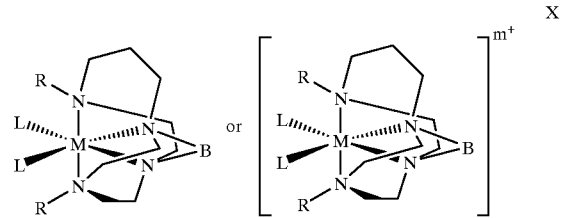

wherein M is a radioactive metal having a valence of 2, +3, +4, or +5; m⁺ designates the charge of the metal complex, each R is independently $C_1$–$C_8$ linear or branched alkyl, and mixtures thereof; wherein B is a bridging unit selected from the group consisting of 2-butenylene, 2,3-dimethylbutenylene, 1,2-xylyl, substituted 1,2-xylyl, and mixtures thereof; L is a pharmaceutically acceptable ligand; X is a pharmaceutically compatible anion in sufficient amount to provide electronic neutrality; and b) the balance a pharmaceutically acceptable carrier.

* * * * *

UNITED STATES PATENT AND TRADEMARK OFFICE
CERTIFICATE OF CORRECTION

PATENT NO. : 6,627,176 B2
DATED : September 30, 2003
INVENTOR(S) : Perkins

It is certified that error appears in the above-identified patent and that said Letters Patent is hereby corrected as shown below:

Title page,
Item [57], ABSTRACT,
Delete

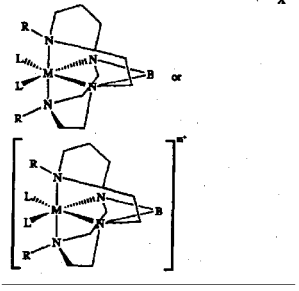

Columns 2 and 3,
Insert --

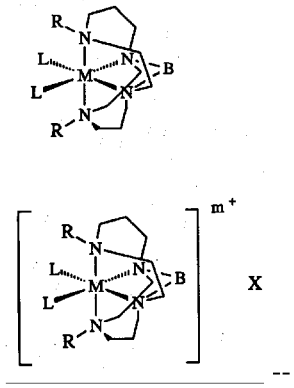

--

Signed and Sealed this

Fourteenth Day of September, 2004

JON W. DUDAS
*Director of the United States Patent and Trademark Office*